(12) United States Patent
Weisse et al.

(10) Patent No.: US 11,826,516 B2
(45) Date of Patent: Nov. 28, 2023

(54) URETERAL BYPASS DEVICES AND PROCEDURES

(71) Applicants: Charles Winston Weisse, New York, NY (US); Allyson Cortney Berent, New York, NY (US)

(72) Inventors: Charles Winston Weisse, New York, NY (US); Allyson Cortney Berent, New York, NY (US)

( * ) Notice: Subject to any disclaimer, the term of this patent is extended or adjusted under 35 U.S.C. 154(b) by 250 days.

(21) Appl. No.: 17/356,644

(22) Filed: Jun. 24, 2021

(65) Prior Publication Data
US 2021/0402136 A1    Dec. 30, 2021

Related U.S. Application Data

(60) Provisional application No. 63/043,270, filed on Jun. 24, 2020.

(51) Int. Cl.
*A61M 25/00* (2006.01)
*A61M 39/02* (2006.01)

(52) U.S. Cl.
CPC ........ *A61M 25/0017* (2013.01); *A61M 39/02* (2013.01); *A61M 2039/0202* (2013.01);
(Continued)

(58) Field of Classification Search
CPC ........ A61M 1/285; A61M 1/284; A61M 1/28; A61M 1/1678; A61M 1/159;
(Continued)

(56) References Cited

U.S. PATENT DOCUMENTS 3,515,124 A * 6/1970 Gurchot ................. A61M 1/70
604/128
3,875,941 A   4/1975 Adair
(Continued)

FOREIGN PATENT DOCUMENTS

CN    210673993    6/2020
EP    1051989      11/2000
(Continued)

OTHER PUBLICATIONS

Dirrig, H. et al., "Diagnostic Imaging Observations in Cats Treated with the Subcutaneous Ureteral Bypass System", Journal of Small Animal Practice, vol. 61, (2020), pp. 24-31.
(Continued)

*Primary Examiner* — Adam Marcetich
(74) *Attorney, Agent, or Firm* — Hartman Global IP Law; Gary M. Hartman; Domenica N. S. Hartman

(57) ABSTRACT

Ureteral bypass devices and procedures for performing internalized urinary diversions within patients. Such a procedure includes implanting a first catheter and securing a distal end of the first catheter within the renal pelvis or ureter of a patient, implanting a cystostomy catheter through and securing a distal end of the cystostomy catheter within the urinary bladder of the patient, fluidically connecting proximal ends of the first and cystostomy catheters to an adapter, and then subcutaneously implanting a sampling/flushing port and fluidically connecting a proximal end of the sampling/flushing port to the adapter via a third catheter to yield an artificial ureteral bypass device, in which the first and cystostomy catheters are fluidically connected together and fluidically connected to the subcutaneously-placed sampling/flushing port.

24 Claims, 7 Drawing Sheets

(52) U.S. Cl.
CPC ............... *A61M 2202/0496* (2013.01); *A61M 2210/1089* (2013.01)

(58) Field of Classification Search
CPC .............. A61M 25/0017; A61M 39/02; A61M 2039/0202; A61M 2202/0496; A61M 2210/1089; A61M 2210/1078; A61M 27/002; A61M 25/04; A61M 39/0208; A61M 2205/04
See application file for complete search history.

(56) References Cited

U.S. PATENT DOCUMENTS

| | | | |
|---|---|---|---|
| 4,057,066 | A | 11/1977 | Taylor |
| 4,397,647 | A | 8/1983 | Gordon |
| 4,610,657 | A | 9/1986 | Densow |
| 4,692,149 | A | 9/1987 | Rosenberg |
| 4,790,809 | A | 12/1988 | Kuntz |
| 4,957,479 | A | 9/1990 | Roemer |
| 5,059,183 | A | 10/1991 | Semrad |
| 5,224,953 | A | 7/1993 | Morgentaler |
| 5,308,318 | A | 5/1994 | Plassche |
| 5,401,257 | A | 3/1995 | Chevalier et al. |
| 5,792,095 | A | 8/1998 | Kissinger |
| 6,039,712 | A | 3/2000 | Fogarty et al. |
| 6,197,005 | B1 | 3/2001 | Gerlach et al. |
| 6,254,589 | B1 | 7/2001 | Raoz |
| 6,364,868 | B1 | 4/2002 | Ikeguchi |
| 6,656,146 | B1 | 12/2003 | Clayman et al. |
| 6,669,708 | B1 | 12/2003 | Nissenbaum |
| 6,685,744 | B2 | 2/2004 | Gellman et al. |
| 6,699,216 | B2 | 3/2004 | Ikeguchi |
| 7,018,384 | B2 | 3/2006 | Skakoon |
| 7,037,345 | B2 | 5/2006 | Bottcher et al. |
| 7,044,981 | B2 | 5/2006 | Liu et al. |
| 7,316,663 | B2 | 1/2008 | Whitmore, III |
| 7,507,218 | B2 | 3/2009 | Aliski et al. |
| 7,513,892 | B1 | 4/2009 | Haaralo et al. |
| 7,722,677 | B2 | 5/2010 | Ward |
| 8,192,500 | B2 | 6/2012 | Chung |
| 10,441,398 | B2 | 10/2019 | Forsell |
| 2002/0045847 | A1 | 4/2002 | Borgesen |
| 2004/0153112 | A1 | 8/2004 | Nissenbaum et al. |
| 2006/0058731 | A1* | 3/2006 | Burnett ............... A61M 1/282 604/29 |
| 2006/0142732 | A1 | 6/2006 | Karmarkar et al. |
| 2006/0200079 | A1 | 9/2006 | Magnusson |
| 2007/0026043 | A1 | 2/2007 | Guan et al. |
| 2007/0049907 | A1 | 3/2007 | Fischer et al. |
| 2007/0060914 | A1 | 3/2007 | Magnusson |
| 2007/0100299 | A1 | 5/2007 | Magnusson |
| 2007/0299409 | A1 | 12/2007 | Whitbourne et al. |
| 2010/0228079 | A1* | 9/2010 | Forsell ............... A61B 5/6885 600/30 |
| 2011/0295178 | A1* | 12/2011 | Albrecht ............... A61F 5/0079 604/8 |
| 2012/0157833 | A1* | 6/2012 | Berent ............... A61B 17/11 600/581 |
| 2013/0211322 | A1* | 8/2013 | Degen ............... A61M 1/28 604/29 |
| 2016/0375190 | A1* | 12/2016 | Blatter ............... A61M 1/1678 604/28 |
| 2017/0021129 | A1* | 1/2017 | Erbey, II ............ A61M 27/008 |
| 2018/0338914 | A1* | 11/2018 | Inhaber ............... A61M 27/002 |

FOREIGN PATENT DOCUMENTS

| | | |
|---|---|---|
| JP | 2019208767 | 12/2019 |
| WO | 2012082990 | 6/2012 |

OTHER PUBLICATIONS

International SearchReport & Written Opinion for International Application No. PCT/US2021/038813, dated Oct. 12, 2021, 11 pages.

Holger Gerullis, Thorsten H. Ecke, Klaus Schwartmann, Christoph J. Heuck, Christoph Elmer, Jens W. Bagner, Sunil Kocheril, and Thomas Otto; Nephrocutaneous Bypass in Ureteral Obstruction, Surgical Techniques in Urology; 2010, 480-485.

Francois Desgrandchamps, Stephane Lerous, Vincent Ravery, Ghislain Bochereau, Philippe Menut, Paul Meria, Philippe Ballanger, and Pierre Teillac; Subcutaneous Pyelovesical Bypass as Replacement for Standard Percutaneous Nephrostomy for Palliative Urinary Diversion: Prospective Evaluation of Patient's Quality of Life; Journal of Endourology; vol. 21, No. 2, Feb. 2007.

A. Jurczok, H. Loertzer, S. Wager, P. Fornara; Subcutaneous Nephrovesical and Nephrocutaneous Bypass; Gynecologic and Obstetric Investigation; 2005; 59: 144-148.

David G. Bell, Marc Anthony Fischer; Palliative Subcutaneous Tunneled Nephrostomy Tube (PSTN): A simple and effective technique for management of malignant extrinsic ureteral obstruction; The Canadian Journal of Urology; Feb. 2002.

Michel E. Jabbour, Francois Desgrandchamps, Emil Angelescu, Pierre Teillac and Alain Le Duc; Percutaneous Implantation of Subcutaneous Prosthetic Ureters: Long-Term Outcome; Journal of Endourology; vol. 15, No. 6, Aug. 2001; 611-614.

Israel Nissenkorn nd Yehoshua Gdor; Nephrovesical Subcutaneous Stent: an Alternative to Permanent Nephrostomy; The Journal of Urology; vol. 163, 528-530, Feb. 2000.

S. Mjinhas, H.C. Irving, S.N. Lloyd, I. Eardley, A.J. Browning and A.D. Joyce; Extra-anatomic stents in ureteric obstruction: experience and complications; BJU International (1999), 84, 762-764.

Francois Desgrandchamps, Olivier Cussenot, Paul Meria, Ariane Cortesse, Pierre Teillac and Alain Le Duc; Subcutaneous Urinary Diversions for Palliative Treatment of Pelvic Malignancies; The Journal of Urology; vol. 154, 367-370, Aug. 1995.

Stephen Y. Nakada, Marshall E. Hicks, Adam J.Gerber, Daniel Picus, J. Stuart Wolf, and Ralph V. Clayman; Subcutaneous Urinary Diversion Utilizing a Nephrovesical Stent: A superior Alternative to Long-Term External Drainage; Urology, Mar. 1995, vol. 45, No. 3.

* cited by examiner

URETERAL BYPASS DEVICES AND PROCEDURES

CROSS REFERENCE TO RELATED APPLICATIONS

This application claims the benefit of U.S. Provisional Application No. 63/043,270 filed Jun. 24, 2020, the contents of which are incorporated herein by reference.

BACKGROUND OF THE INVENTION

The present invention generally relates to devices and procedures suitable for treating patients having ureteral obstructions or the like. More particularly, this invention relates to a ureteral bypass device and procedures for implanting the device, for example, by placing the device under the skin (subcutaneously) or within the abdominal cavity (intra-abdominally) of a patient. The device utilizes catheters and locking/retention mechanisms adapted to retain distal ends of the catheters within the renal pelvis and urinary bladder to avoid inadvertent dislodgement, as well as provide a seal to the kidney and bladder tissues to prevent urine leakage after device placement. The device further includes a port and reservoir that enable and facilitate sampling, flushing, and testing the entire device for diagnostic or therapeutic purposes, without the need for invasive and expensive diagnostic methods.

Ureteral obstructions are a major surgical and endourological problem in both human and veterinary medicine. These obstructions can occur for various reasons, the most common of which include but are not limited to ureterolithiasis, urinary tract (intrinsic) or extrinsic neoplasia, and ureteral strictures. The traditional treatment in human medicine has involved the use of minimally invasive endourological procedures, for example, ureteral stenting, lithotripsy, ureteroscopic laser ablation, laparoscopic ureteral resection and anastomosis, and ureteropyelotomy. Minimally invasive treatments have nearly replaced open surgical procedures. In contrast, open surgical procedures such as ureterotomy, ureteral reimplantation and ureteronephrectomy are routinely performed for most causes of ureteral obstructions in companion animals (for example, canine and feline) due to the small nature of the canine (about 1 to 2 mm) and feline (about 0.3 to 0.4 mm) ureters and the minimal options available for interventional devices in animals of this size. Recently, the development of feline and canine double-pigtail ureteral stents has occurred, and interventional treatments have become progressively more available in larger patients. Unfortunately, situations arise, particularly in small pediatric and veterinary patients, in whom ureteral decompression is necessary but traditional surgery or endourological procedures are associated with excessive morbidity or mortality, are impossible due to the size or anatomy, or are contraindicated.

In human medicine, if diversion procedures fail, implantation of an externalized percutaneous nephrostomy tube is usually necessary to provide either temporary or long-term drainage of the renal collection system. Placement of an externalized percutaneous nephrostomy tube is also possible in veterinary and pediatric patients for in-hospital stabilization but is not feasible for long-term use. Major disadvantages associated with long-term use include the need for regular catheter exchanges, the risk of urinary tract infections, urinary leakage and catheter dislodgement, social embarrassment, discomfort, and an impaired quality of life reported for patients. Subcutaneous (or intra-abdominal) urinary diversion devices can internalize a nephrostomy catheter and allow the urine to drain to the urinary bladder through a subcutaneous or intra-abdominal catheter. This eliminates most of the major disadvantages associated with externalized nephrostomy catheters because infection, regular nursing care, leakage, dislodgement, and an impaired quality of life are no longer prominent issues. Subcutaneous or intra-abdominal urinary diversion (bypass) devices have become a more useful solution for patients with very complicated medical problems for whom externalized catheters are not a realistic option outside of a hospital setting.

A few variations on ureteral bypass devices have been reported in the past, varying from non-locking pigtail catheters, non-fenestrated double-pigtail stents, and non-locking double-lumen catheters with an inner silicone tube and an outer polyester sheath. For example, such devices have been reported or offered by Coloplast A/S (Pyelovesical Bypass). These various devices have been placed subcutaneously with surgical approaches requiring suturing of the tube to the bladder wall and renal capsule to prevent dislodgement and leakage. Short-term and long-term complications have been reported, with the major concerns being infection (46%), bleeding/hematoma (38%), discomfort (31%), occlusion (encrustation) (23%), and kinking (8%) (Wrona et al. 2017). However, these devices remain promising when all other traditional options have failed.

There is an ongoing need for devices that can treat various causes of ureteral obstruction, regardless of etiology, patient species, or size, in a rapid, simple, safe, and effective manner. In particular, there is a need for a ureteral bypass device capable of overcoming the shortcomings of the prior art, particularly infection, discomfort, invasiveness, the large size of the device, occlusion via encrustation, or kinking of the device.

A subcutaneous ureteral bypass (SUB) device disclosed in U.S. Pat. No. 8,808,261 to Berent et al. has solved some of the problems with previous techniques for providing urinary drainage due to ureteral obstruction. This device has been reported to function well with minimal complications compared to traditional surgery or ureteral stent placement. The most common complications encountered have included occlusion/encrustation (approximately 24%), chronic infections (approximately 13%), and tube kinking when passing through the body wall (at least 15%), not unlike some of the complications encountered with the pyelovesical bypass device.

BRIEF DESCRIPTION OF THE INVENTION

The present invention provides a ureteral bypass device and procedure suitable for performing internalized urinary diversions within patients, including large patients such as human adults, as well as small patients such as children and animals, even when growth is anticipated.

According to a first aspect of the invention, the procedure includes creating an incision in the patient, implanting a first catheter and securing a distal end of the first catheter within the renal pelvis or ureter of a patient, implanting a cystostomy catheter through the incision and securing a distal end of the cystostomy catheter within the urinary bladder of the patient, fluidically connecting proximal ends of the first and cystostomy catheters to an adapter (Y-connector for a single kidney; X-connector for both kidneys), and then subcutaneously implanting a sampling/flushing port and fluidically connecting a proximal end of the sampling/flushing port to the adapter via a third catheter to yield an artificial ureteral bypass device, in which the first and cystostomy catheters are fluidically connected together and fluidically connected to the subcutaneously-placed sampling/flushing port. The incision is then closed. The subcutaneously-placed sampling/flushing port has a septum that defines an entry site of the subcutaneously-placed sampling/flushing port and is accessible through the skin of the patient to provide means for performing diagnostic and therapeutic procedures, and the third catheter defines a non-dynamic volume between the adapter and the sampling/flushing port through which urine does not flow so that the non-dynamic volume serves as an anti-infection, anti-encrustation reservoir.

According to a second aspect of the invention, an artificial ureteral bypass device includes a nephrostomy catheter having a proximal end, an oppositely-disposed distal end, and means for securing the distal end within the renal pelvis of a kidney of a patient, a cystostomy catheter having a proximal end, an oppositely-disposed distal end, and means for securing the distal end of the cystostomy catheter within the urinary bladder of the patient, an adapter (either a Y-connector for a single kidney, or an X-connector for both kidneys) fluidically connected to the proximal ends of the nephrostomy and cystostomy catheters, and a sampling/flushing port that is fluidically connected to the adapter via a third catheter. The nephrostomy and cystostomy catheters are fluidically connected together through the adapter without any subcutaneous connection and are fluidically connected to the sampling/flushing port. The sampling/flushing port defines an entry site that is accessible through the skin of the patient when the sampling/flushing port is subcutaneously placed to provide means for performing diagnostic and therapeutic procedures, and the third catheter defines a non-dynamic volume between the adapter and the sampling/flushing port through which urine does not flow so that the non-dynamic volume defines as an anti-infection, anti-encrustation reservoir.

A technical effect of the invention is that the device is capable of use in the treatment of many, if not all, causes of ureteral obstruction, regardless of etiology, patient size or species. The subcutaneously-placed sampling/flushing port and its entry site can be placed so that the entry site is accessible for testing, sampling and flushing of the device, and therefore enables occlusions, encrustation, and the like to be cleared or avoided without necessitating the removal of the device from the patient or the need for future surgical manipulation. Additionally, the port and its fluidic connection to the adapter (e.g., a catheter) in combination create a relatively large internal and non-dynamic reservoir for fluids/medications introduced into the device via the entry site of the port, for example, flushing fluids introduced for the purpose of treating or clearing occlusions and encrustation and antiseptic fluids for treating infections. The device is also well suited for remaining indwelling long-term within a patient, preferably for periods of at least 36 months but often much longer extended to the life of the patient. In young children with anatomical anomalies, this allows the time for the urinary system to grow prior to the consideration of more dramatic reconstructive surgeries that would ideally be done at an older age.

Other aspects and advantages of this invention will be appreciated from the following detailed description.

DETAILED DESCRIPTION OF THE INVENTION

Figure 1:
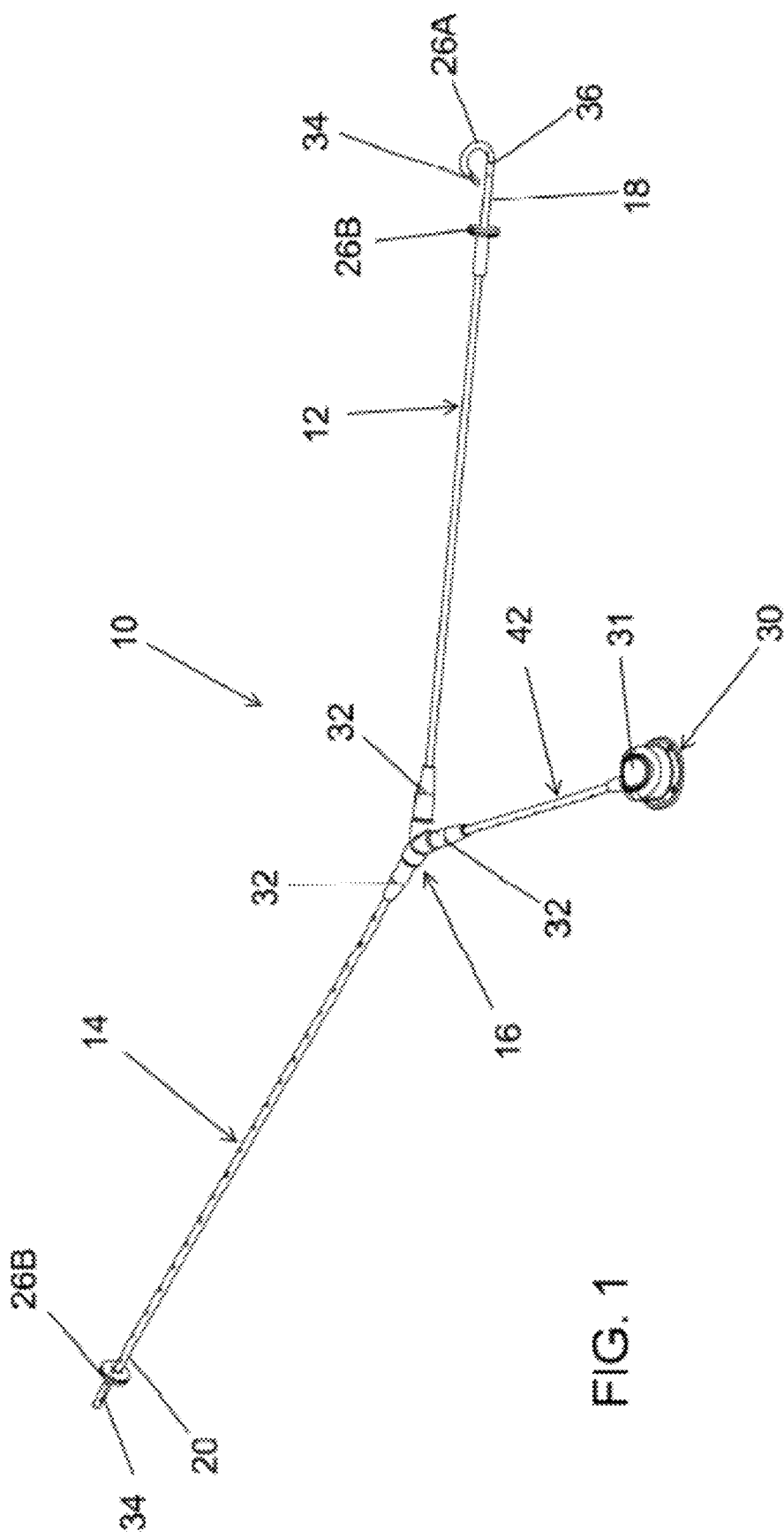
FIG. 1 is a perspective view of an artificial ureteral bypass device comprising nephrostomy (or ureterostomy), cystostomy, and port catheters in accordance with a first nonlimiting embodiment of this invention.

The intended purpose of the following detailed description of the invention and the phraseology and terminology employed therein is to describe what is shown in the drawings, which include the depiction of one or more nonlimiting embodiments of the invention, and to describe certain but not all aspects of the embodiment(s) depicted in the drawings. The following detailed description also identifies certain but not all alternatives of the depicted embodiment(s). Therefore, the appended claims, and not the detailed description, are intended to particularly point out subject matter regarded as the invention, including certain but not necessarily all of the aspects and alternatives described in the detailed description.

The embodiments depicted in the drawings will be referred to as ureteral bypass devices (UBD) that are capable of treating causes of ureteral obstruction. The devices can be used in humans (children and adults) and animals, regardless of etiology, species, or patient size, and can be optimized for the patient. In addition, the UBDs of this invention beneficially allow for secure and facile placement of the devices within a patient, as will be evident from the following discussion.

Figure 2:
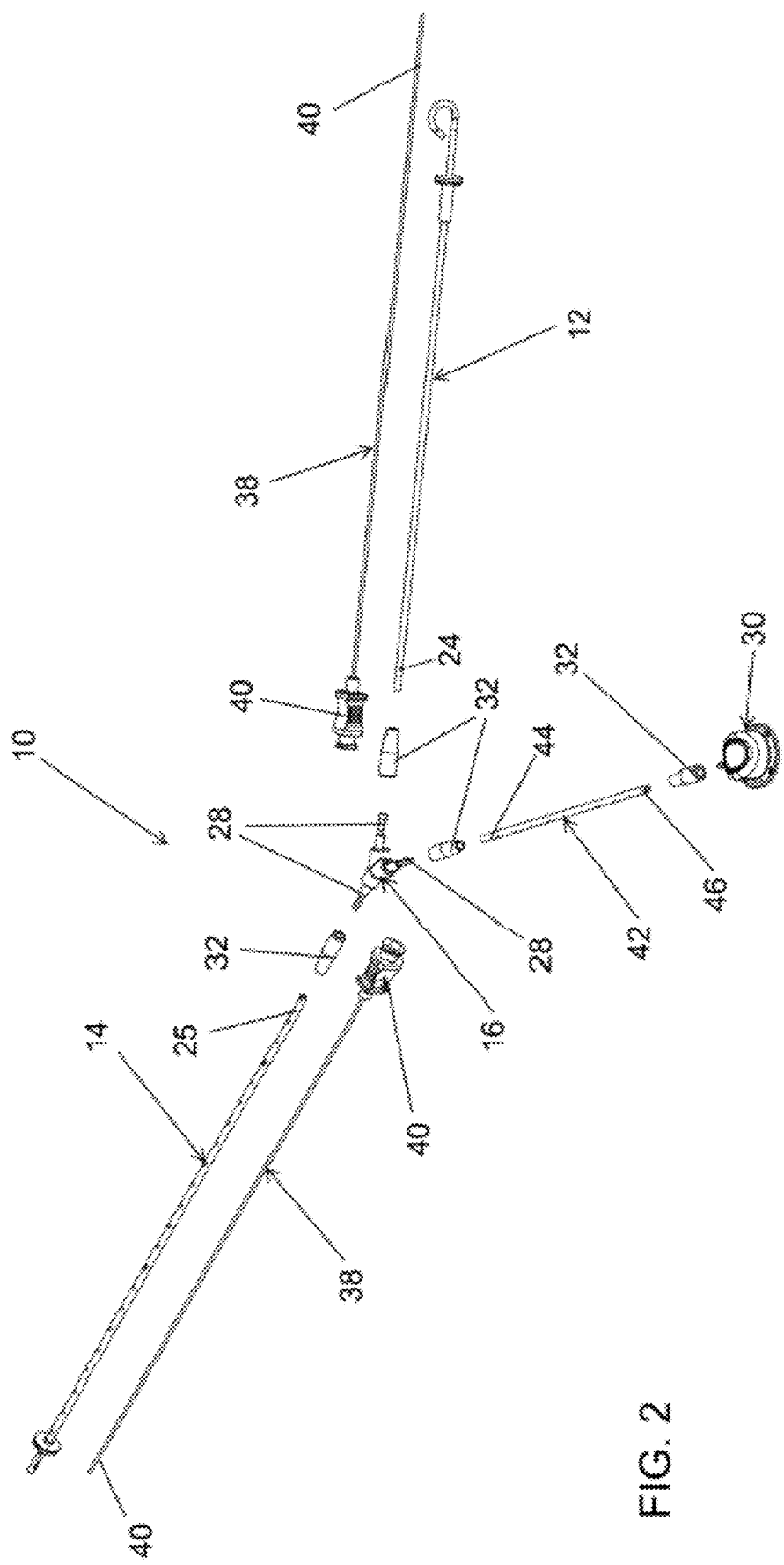
FIG. 2 is an exploded view of the device of FIG. 1.

FIGS. 1 and 2 represent a first nonlimiting embodiment of a UBD 10 as comprising a pair of catheters 12 and 14 and an adapter 16 to which the catheters 12 and 14 are coupled. Distal ends 18 and 20 of the catheters 12 and 14 (i.e., remote from the adapter 16) are adapted to be placed within, respectively, the renal pelvis (or ureter) and urinary bladder of a patient. As such, the catheters 12 and 14 can be referred to as nephrostomy (or ureterostomy) and cystostomy (or bladder) catheters, respectively, though it should be evident that the catheters 12 and 14 are configured differently from prior art catheters of types used in ureteral bypass procedures. Suitable sizes for the catheters 12 and 14 will depend on the size of the patient and the drainage requirements. The diameters of the catheters 12 and 14 are preferably larger than traditional ureteral stents (limited by natural ureteral size) to provide better drainage. As nonlimiting examples, catheter sizes of 5 to 6 Fr will typically be suitable for cats, 6 Fr will typically be suitable for dogs, 5 to 10 Fr will typically be suitable for children and adults, though larger sizes (for example, 5 to 30 Fr) are possible and could be used if necessary. The lengths of the catheters 12 and 14 can also be tailored or trimmed to meet the particular requirements of a patient.

Figure 5:
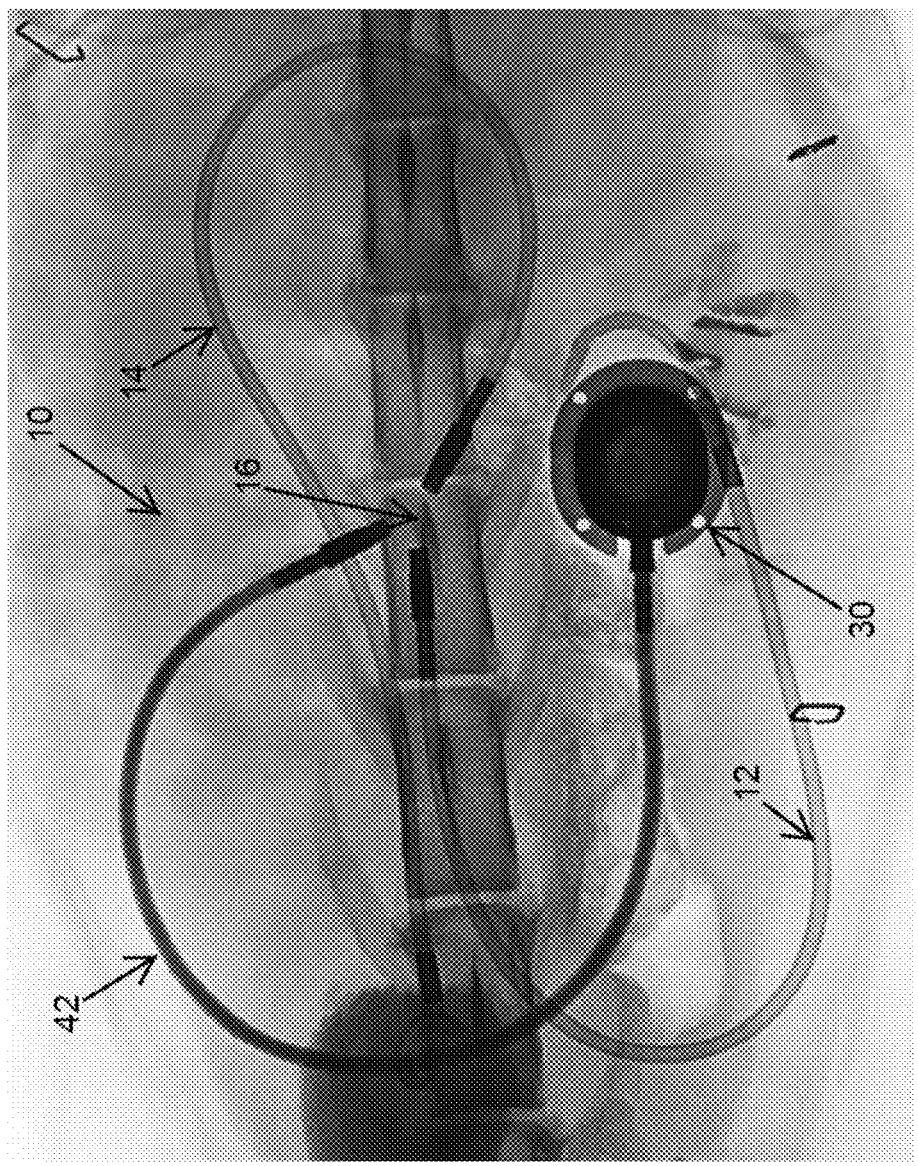
FIG. 5 is an image showing the artificial ureteral bypass device of FIGS. 1 and 2 implanted in a feline patient.

Each catheter 12 and 14 may be equipped with a locking mechanism that retains its respective distal end 18 and 20 within the renal pelvis or urinary bladder of the patient, respectively. As represented in FIGS. 1 and 2, the distal end 18 of the nephrostomy catheter 12 may be configured as a locking loop (pigtail) 26A capable of retaining the distal end 18 within the renal pelvis of a kidney for nephrostomy placement. To keep the locking loop 26A coiled after being placed inside the renal pelvis, a string (not shown) may be passed inside the catheter 12 from its locking distal end 18 and through a proximal end 24 of the catheter 12 at which the catheter 12 will be connected to the adapter 16 (FIGS. 1 and 2). For example, the catheter 12 may be fluidically connected to the adapter 16 via one of three male fittings 28 of the adapter 16 (FIG. 2), to which the catheter 12 is secured with a boot 32 to prevent leaks at the catheter/adapter interface. The boot 32 is preferably formed of a biocompatible material, for example, silicone. The locking configuration shown for the distal end 18 in FIGS. 1 and 2 can be maintained by entrapping the string between the proximal end 24 of the catheter 12 and the fitting 28 (represented in FIG. 2 as a graduated barb). Alternatively, the catheter can be passed down the ureter (ureterostomy catheter) when the renal pelvis is small (FIG. 5).

Similar to the nephrostomy catheter 12, the proximal end 25 of the cystostomy catheter 14 may be fluidically connected to the adapter 16 via a second of the male fittings 28 of the adapter 16, and secured thereto with a boot 32 formed of a biocompatible material, for example, silicone. The distal end 20 of the cystostomy catheter 14 may be configured as a locking loop (pigtail) similar to the nephrostomy catheter 12 and its distal end 18. Alternatively, FIGS. 1 and 2 represent the catheter 14 as a straight catheter with a fenestrated tip comprising at least one fenestration 34 and a cuff 26B adapted for adherence to the external serosal surface of a bladder. A particular example is a silicone catheter with a DACRON® cuff (or any other adhered material) 26B for organ pexy to prevent leakage and ensure stability. As represented in FIGS. 1 and 2, the nephrostomy catheter 12 can also be equipped with a cuff 26B, wherein the cuff 26B can be provided instead of, or in addition to, the locking loop 26A. The addition of a cuff 26B to each catheter 12 and 14 can be advantageous, in that the cuff 26B is able to form a secure adhesion without the need for direct attachment to the body wall for the kidney or urinary bladder (nephropexy or cystopexy), and in this manner promotes the ability of the catheters 12 and 14 to remain secure to the kidney capsule and bladder wall (serosa) and prevent leakage of urine during healing. The distal end 18 of the catheter 12 is also represented as fenestrated, in this case, with multiple fenestrations 34. As is visible for the catheter 12 in FIGS. 1 and 2, a radio-opaque marker band 36 can be placed behind the last (most proximal) fenestration 34 to allow for fluoroscopic assurance that the entire loop 26A and all fenestrations 34 are within the renal pelvis to prevent any extravasation or leakage of urine.

FIGS. 1 and 2 further depict the UBD 10 as comprising a third catheter 42 having a proximal end 44 fluidically connected to the adapter 16 via a third of the male fittings 28, and secured thereto with a boot 32 formed of a biocompatible material, for example, silicone. The catheter 42 further has a port 30 at a distal end 46 thereof (i.e., remote from the adapter 16), and as such may be referred to herein as the port catheter 42. The port 30 is represented in FIGS. 1 and 2 as configured as a sampling and/or flushing (hereinafter, "sampling/flushing") port with an entry site 31, though from the following discussion it will become apparent that certain features of the port 30 would not be necessary in all embodiments of the invention.

Figure 3:
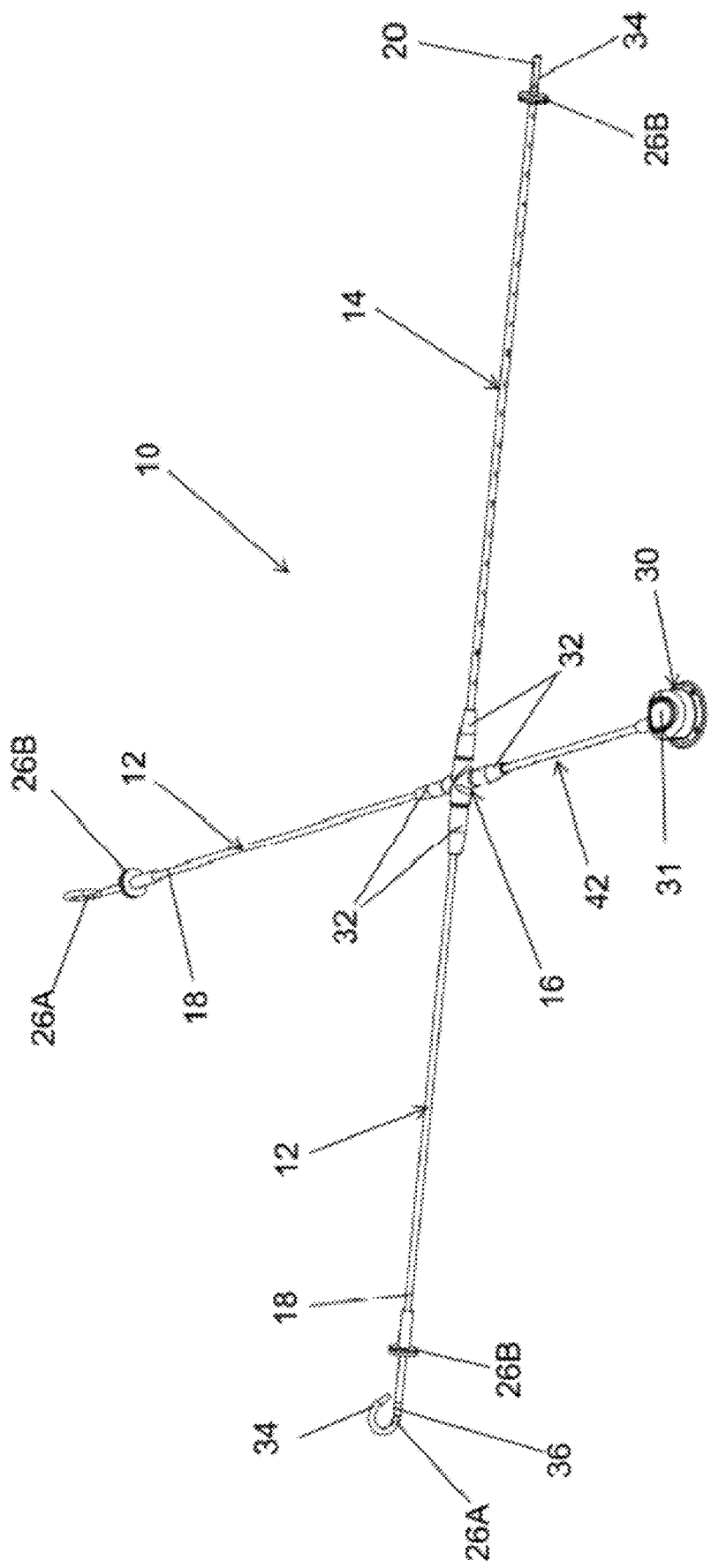
FIG. 3 is a perspective view of an artificial ureteral bypass device comprising nephrostomy (or ureterostomy), cystostomy, and port catheters in accordance with a second nonlimiting embodiment of this invention.
Figure 4:
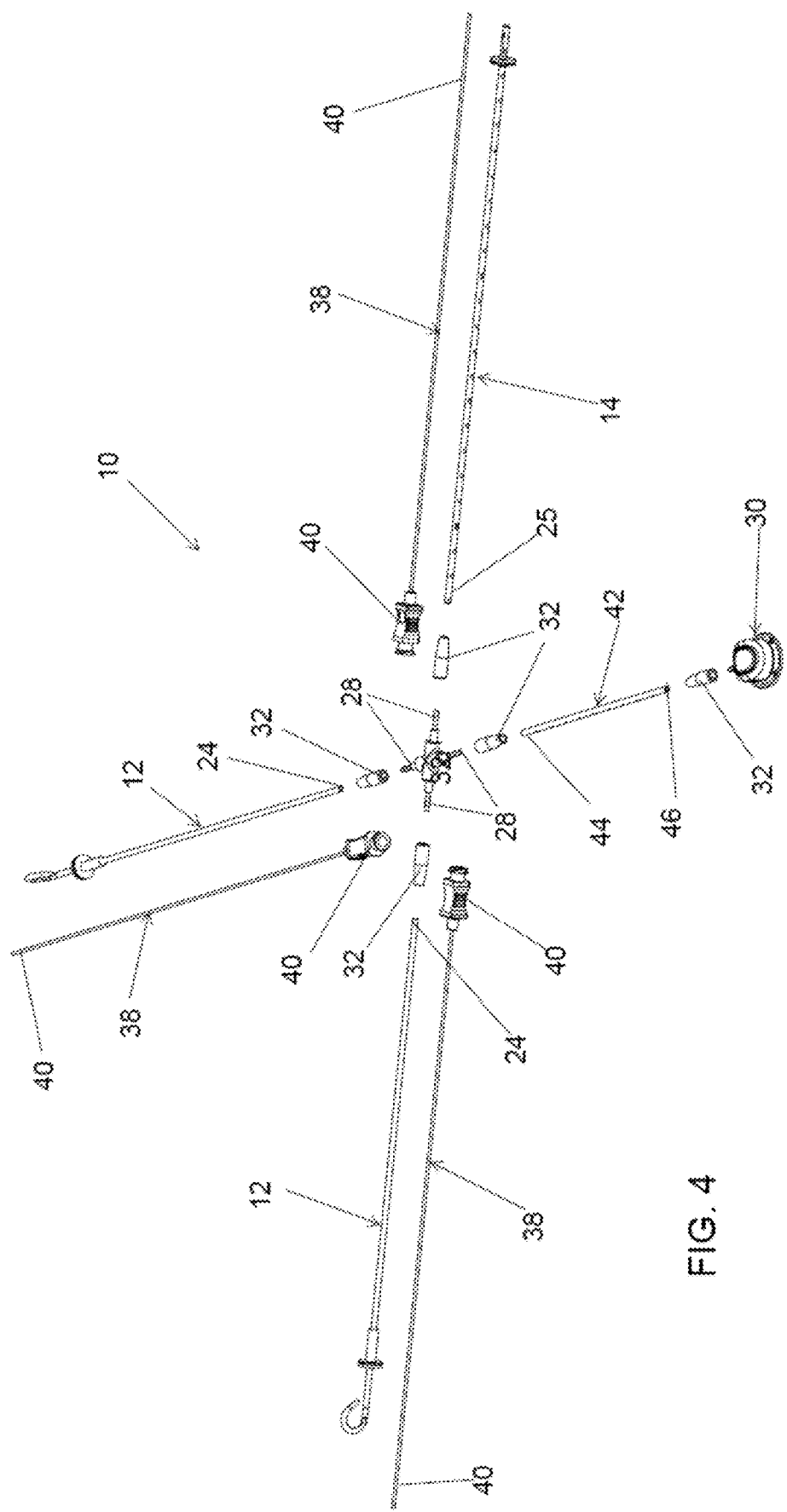
FIG. 4 is an exploded view of the device of FIG. 3.

FIGS. 1 and 2 represent the catheters 12, 14, and 42, the adapter 16, and the port 30 as separate components that must be assembled, though it is also within the scope of the invention that the UBD 10 could be manufactured as a single unitary component. In either case, the catheters 12 and 14 and adapter 16 are adapted to be entirely implanted within a patient, in particular, within the abdominal cavity (intraabdominally) of a patient, whereas the port 30 and a distal portion of the port catheter 42 are not placed in the abdominal cavity but instead are placed subcutaneously. The fittings 28 of the adapter 16 are represented in FIG. 2 as male barbed fittings configured to provide male-to-male couplings with the catheters 12, 14, and 42, and are therefore preferably sized to correspond to the size of the catheters 12, 14, and 42 and drainage requirements of the UBD 10. In the embodiment of FIGS. 1 and 2, the adapter 16 is equipped with three fittings 28, one for each of the catheters 12, 14, and 42, so that the cystostomy catheter 14 fluidically communicates with a single nephrostomy catheter 12 through the adapter 16 and the port 30 communicates with both catheters 12 and 14 through the adapter 16. As seen in FIGS. 3 and 4, the adapter 16 can be equipped with additional fittings 28, for example, a fourth fitting 28 that enables a second nephrostomy catheter 12 to be coupled to the adapter 16, such that the UBD 10 can be implanted in the renal pelvis (or ureter) of each kidney of the patient and the cystostomy catheter 14 fluidically communicates with both nephrostomy catheters 12 (in the event of a bilateral ureteral obstruction). Advantageously, such a four-way design for the adapter 16 eliminates the requirement in prior bilateral ureteral bypass procedures to implant two separate cystostomy catheters when necessary.

As a result of being placed subcutaneously, the port 30 provides a subcutaneous access to the port catheter 42, which is fluidically coupled to the catheters 12 and 14 via the adapter 16. The subcutaneous port 30 allows for testing, sampling and flushing of the UBD 10, and therefore enables occlusions, encrustation, and the like to be cleared or avoided. A benefit of the port 30 and its entry site 31 is that they allow for the UBD 10 to be tested using contrast material and fluoroscopic guidance to ensure the patency of the system, as well as for urine sampling of the system directly, in a sterile manner. The entry site 31 of the port 30 is preferably configured as a septum that can be punctured by a needle, for example, a Huber point non-coring needle, which enables for multiple sampling and needle access without leakage. The port 30 is placed subcutaneously so that its entry site 31, and particularly its septum, is in proximity to the patient's skin. As with ports employed with implantable venous access systems, the septum can be made of a self-sealing silicone rubber that can be punctured numerous and preferably thousands of times. Through the entry site 31, the UBD 10 can be tested, such as with a contrast material and fluoroscopy to ensure patency and no leakage, sampled for infection, urinalysis, etc., and flushed if an occlusion is determined to exist within the catheters 12 and 14 or the adapter 16. If encrustation or occlusion has occurred, a needle can be used to inject a contrast material into the adapter 16 via placing the needle through the patient's skin, through the entry site 31 of the port 30, and from there instilled in the catheters 12 and 14 via the port catheter 42 and adapter 16 to enable documentation of the occlusion site, all while the patent is awake. The entire UBD 10 can then be flushed of debris through the entry site 31 of the port 30 to remove the occlusion. Access to the UBD 10 through the entry site 31 is able to promote the safety and effectiveness of long-term management of the UBD 10 without necessitating the need for testing using an invasive procedure, such as renal puncture. Furthermore, the ability to flush the entire UBD 10 of debris to remove an occlusion is not only diagnostically beneficial, but can also be potentially therapeutic for the patient using antibiotics, disinfectants, or anti-encrustation materials.

An important benefit of the port 30 and its port catheter 42 is that they define in combination a relatively large internal reservoir for fluids/medications introduced into the UBD 10 via the entry site 31, for example, flushing fluids introduced for the purpose of treating or clearing occlusions and encrustation and antiseptic fluids for treating infections. In particular, the combined internal volume of the port 30 and port catheter 42 is outside the urine flowpath within the catheters 12 and 14, and is preferably sized to retain a portion of the flushing (or other) fluid so that the fluid is not subject to being quickly flushed through the catheters 12 and 14 as a result of urine flow. As such, the retained portion continues to be dispensed from the port 30 and port catheter 42 to the catheters 12 and 14 to provide a residual benefit to the patient. This capability is believed to be particularly beneficial for reducing the incidence of complications such as occlusions, encrustations, and chronic infections. This is demonstrated in FIG. 5 wherein the contrast material remains within the port 30 and port catheter 42 but has been flushed out of the catheters 12 and 14 due to the urine flowpath. The reservoir of contrast could be disinfectant or other medications preventing ascending infections (from port access) or encrustation.

A preferred procedure for placing the UBD 10 within a patient is to use a modified version of the well-known modified-Seldinger technique utilizing a guidewire and preferably under fluoroscopic guidance. Alternatively, a direct-stick method can be performed without guidewire access. Using a modified-Seldinger technique, an incision is made at a sterilized site through which the components of the UBD 10 will be implanted. It is not necessary to implant the completed assembly for the UBDs 10 shown in FIGS. 1-4, but instead, the catheters 12, 14, and 42, adapter 16, and port 30 can be implanted separately (if not manufactured as a unitary component). Punctures can be made in each of the renal pelvis and the urinary bladder with separate renal access needles (not shown), suitably sized for the desired guidewire size (typically an 18-gauge renal access needle with a 0.035" guidewire). For both nephrostomy (ureterostomy) and cystostomy placement, a guidewire can then be advanced through the access needle and coiled inside the renal pelvis (or ureter) or urinary bladder. The access needle is then removed over the wire and the distal ends 18 and 20 of the catheters 12 and 14 can be respectively placed over the wire, inside the renal pelvis and urinary bladder. Each catheter 12 and 14 is preloaded with a hollow trocar 38 (FIGS. 2 and 4) to maintain the stiffness and pushability to advance the respective catheter 12/14 over the wire. Whether the patient is human or animal, if the distal end 18 of the nephrostomy catheter 12 is configured as a locking loop 26A, the renal pelvis is preferably dilated to accommodate the locking loop 26A. The uncoiled catheter 12 could also be advanced over the guidewire down the ureter in cases with small renal pelvises. An alternative is to use the hollow trocar 38 with a sharp stylette 40 (the sharp tip and cap of which are seen in FIGS. 2 and 4) to directly puncture the renal pelvis or urinary bladder without the use of the modified-Seldinger technique or need for a guidewire.

The distal end 18 of the nephrostomy catheter 12 can then be actuated with a string to form the locking loop 26A, which prevents the catheter 12 from becoming dislodged once placed within the patient. Similarly, the distal end 20 of the cystostomy catheter 14 is secured with the cuff 26B (or, if so equipped, a locking loop 26A) to prevent the catheter 14 from becoming dislodged from the urinary bladder. Both catheters 12 and 14 can be cut to an appropriate length, based on patient needs, prior to being fluidically connected to the adapter 16 via the fittings 28. The boots 32 can then be advanced onto the proximal ends 24 and 25 of the catheters 12 and 14 to connect and secure the catheters 12 and 14 to the adapter 16 (e.g., the Y-connector of FIGS. 1 and 2 or the X-connector of FIGS. 3 and 4). The locking string(s) of the catheter(s) 12 and/or 14 are further secured to the adapter 16 by advancing the fittings 28 into the catheters 12 and 14. The additional port catheter 42 is similarly attached the remaining fitting 28 of the adapter 16, passed through the body wall, and attached to the port 30, which can then be implanted and secured under the skin to subcutaneous tissue, after which the incision can be closed. As previously noted, the incision is preferably closed so that the entry site 31 of the port 30 is accessible through the patient's skin with simple needle access. The completed assembly of the UBD 10 is entirely located internally of the patient, with the catheters 12 and 14 and the adapter 16 placed completely intra-abdominal, with only the port 30 and a distal portion of its port catheter 42 located subcutaneously at the surface of the abdominal wall. The entry site 31 is accessible through the patient's skin to provide a leak-free access port for testing, sampling and flushing of the UBD 10 with an appropriate needle, such as a non-coring Huber needle.

From the above, it should be appreciated that the present invention provides for facile and secure implantation of the UBD 10 within a patient. The UBD 10 provides the capability for easy sampling of the UBD 10 for infection, urinalysis, or the like, allows for testing the entire UBD 10 with contrast material to ensure patency and no leakage. The UBD 10 can also be flushed if an occlusion is discovered within the UBD 10, or serially to prevent an occlusion. Needle access directly into this UBD 10 (via the entry site 31) makes long-term management of the UBD 10 safe, non-painful, non-invasive, and effective without the requirement for risky, invasive testing procedures that provide only diagnostic utility without any therapeutic options. In patients that require bilateral diversion (about 10 to 30%, depending on cause), the adapter 16 equipped with for four fittings 28 (FIGS. 3 and 4) allows a second nephrostomy catheter 12 to be connected to the single cystostomy catheter 14 through the adapter 16. As a result, only a single access point is required to the urinary bladder, and less artificial material is implanted in the patient.

The most common complications reported for prior pyelovesical bypass and subcutaneous ureteral bypass devices include encrustation, infection, bleeding/hematoma, and kinking. There are considerable advantages of the UBDs 10 represented in FIGS. 1-4 over such devices.

Figure 6:
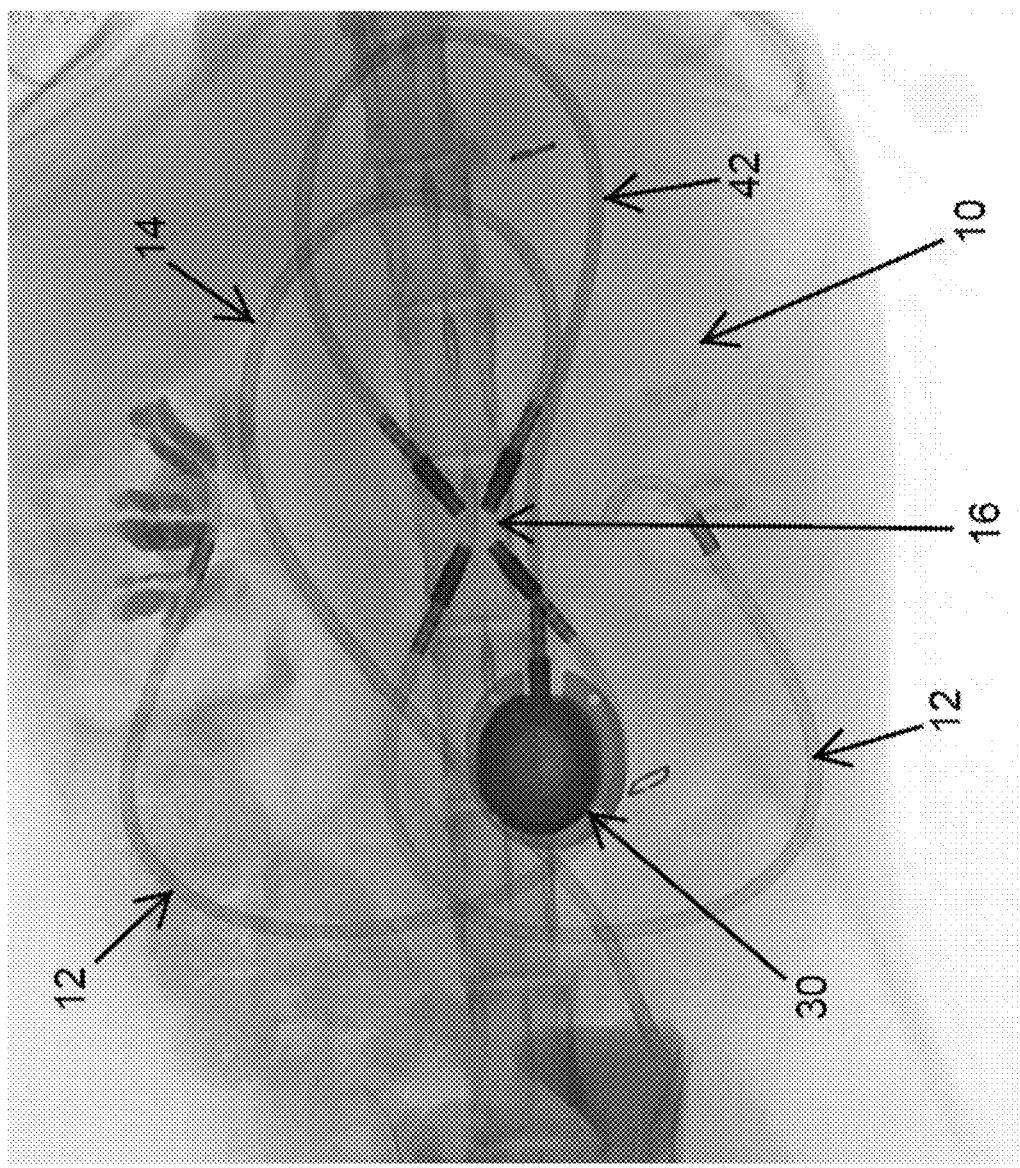
FIG. 6 is an image showing the artificial ureteral bypass device of FIGS. 3 and 4 implanted in a feline patient. Contrast of the port catheter remains while contrasts of the nephrostomy and cystostomy catheters flush out, demonstrating non dynamic fluid flow of the port catheter that enables the retention of antiseptics and anti-encrustation fluids and their slow entry into the urine stream to prevent infections and encrustations.

Encrustation: Pyelovesical bypass and subcutaneous ureteral bypass devices have urine flowing directly through the device with no ability to instill antiseptics that would not be immediately washed through the device with passing urine. Additionally, existing subcutaneous ureteral bypass devices have urine flowing through a shunting port within which inevitably contains regions of slower flow and stagnation where there are opportunities for mineral debris to settle out and accumulate. The UBDs 10 described herein, with a separate port catheter 42 attached to the port 30, allow a non-dynamic segment of catheter volume to retain anti-encrustation substances, such as Tetra-edta, within it (similar to a catheter lock), such that the flow of urine does not flush out this medication. This reduces the chances of catheter and port encrustation. FIGS. 5 and 6 are ventrodorsal radiographs showing the UBDs 10 of FIGS. 1 and 2 and FIGS. 3 and 4, respectively, implanted in patients, and FIG. 5 shows contrast retained within the port catheter 42 because no urine flow occurs within the port catheter 42.

Infection: Pyelovesical bypass and subcutaneous ureteral bypass devices report chronic infections as a complication. For subcutaneous ureteral bypass devices, it is believed infections are introduced through needle access to a subcutaneous sampling/flushing port when traversing the skin. Even when antibiotics or antiseptics are injected into a sampling/flushing port, the flow or urine quickly flushes the medications from the nephrostomy and cystostomy catheters. The UBDs 10 described herein, with a separate port catheter 42 attached to the port 30, allows the non-dynamic segment of volume of the port catheter 42 to retain a portion of the antibacterial substances to reduce the chances of introducing infections into the system.

Hemorrhage: Pyelovesical bypass and subcutaneous ureteral bypass devices are passed subcutaneously. This involves considerable subcutaneous dissection that results in risk of patient discomfort and hemorrhage/hematoma formation. The UBDs 10 described herein require considerably less subcutaneous dissection to accommodate the sampling/flushing port 30.

Catheter Kinking with Obstruction: Pyelovesical bypass and subcutaneous ureteral bypass devices are passed through the abdominal wall. This allows patient repositioning and muscle tone to possibly result in kinking of the nephrostomy and cystostomy catheters that can obstruct urine flow and lead to the original symptoms that prompted placement of the device in the first place. The UDSs 10 described herein have an artificial ureteral bypass portion of the device (catheters 12 and 14) retained entirely within the abdominal cavity; and only a portion of the port catheter 42 connecting to the adapter 16 is passed through the abdominal wall. This important difference resolves the concern about positional kinking of the UBDs 10 as it does not disrupt urine flow from the kidney to the urinary bladder.

Figure 8:
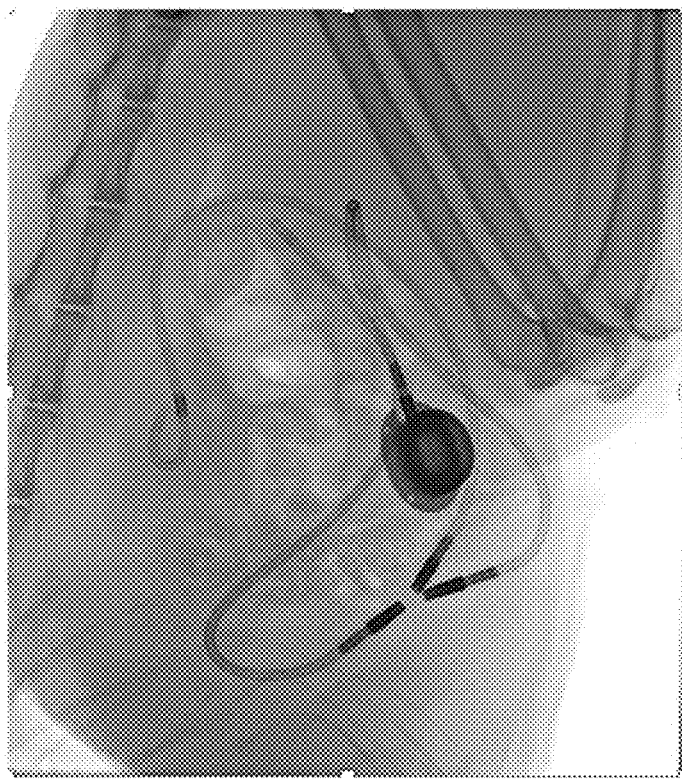
FIGS. 7 and 8 are images of a feline patient with the artificial ureteral bypass device of FIGS. 1 and 2 implanted, with the legs of the feline patient extended and flexed, respectively, and evidencing no kinks in the catheters of the device.
Figure 7:
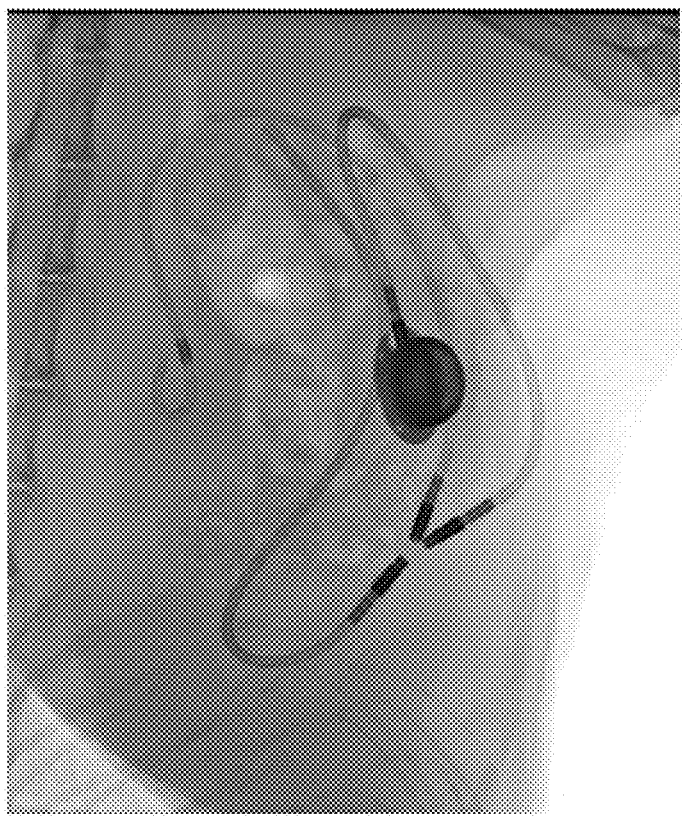

A UBD 10 of the type described herein has been trialed in thirty feline patients and multiple canine patients for various causes of ureteral obstruction. The trials showed the UBD 10 to be successful and patent for urinary drainage long-term with very few associated complications. None of the devices developed intractable encrustation or occlusion, none developed kinking leading to obstruction, or and there were no incidences of dislodgement in the long-term with the practice of serial flushing (every 3-6 months when necessary on an out-patient basis). FIGS. 7 and 8 are images of one feline patient with the artificial ureteral bypass device of FIGS. 1 and 2 implanted, with the legs of the patient extended and flexed, respectively, and evidencing no kinks in the catheters of the device.

While the invention has been described in terms of particular but nonlimiting embodiments, it is apparent that other forms could be adopted by one skilled in the art. For example, the ureteral bypass devices could differ in appearance and construction from the embodiments disclosed, the functions of each component of the devices could be performed by components of different construction but capable of a similar (though not necessarily equivalent) function, and appropriate materials could be substituted for those noted. Therefore, the scope of the invention is to be limited only by the claims.

The invention claimed is:

1. A procedure for performing an internal urinary diversion, the procedure comprising:
   creating an incision in the skin of a patient;
   implanting a first catheter through the incision and securing a distal end of the first catheter within the renal pelvis or ureter of the patient, wherein the first catheter is a nephrostomy or ureterostomy catheter;
   implanting a cystostomy catheter through the incision and securing a distal end of the cystostomy catheter within the urinary bladder of the patient;
   implanting an adapter within the abdominal cavity (intra-abdominally) of the patient through the incision and fluidically connecting proximal ends of the first and cystostomy catheters to the adapter so that the first and cystostomy catheters are fluidically connected together through the adapter;
   implanting a third catheter and a sampling/flushing port that comprises a septum, the third catheter fluidically connecting the sampling/flushing port to the adapter to yield an artificial ureteral bypass device, in which the first and cystostomy catheters are fluidically connected together and fluidically connected to the sampling/flushing port with the adapter, the first and cystostomy catheters and the adapter are completely within the abdominal cavity and together define a urine flowpath that is entirely within the abdominal cavity, the sampling/flushing port and a distal portion of the third catheter are placed subcutaneously and are not placed in the abdominal cavity, the third catheter and the sampling/flushing port are outside the urine flowpath and each has an internal volume that is outside the urine flowpath, and the internal volumes of the third catheter and the sampling/flushing port define a non-dynamic volume that is between the adapter and the septum of the sampling/flushing port and outside the urine flowpath; and
   closing the incision so that the septum of the sampling/flushing port defines an entry site of the sampling/flushing port and is accessible through the skin of the patient to provide means for performing diagnostic and therapeutic procedures; wherein:
   urine does not flow through the non-dynamic volume; and
   at least a portion of a fluid introduced into the artificial ureteral bypass device through the entry site is retained within the non-dynamic volume outside of the urine flowpath, is not subject to being flushed through the first and cystostomy catheters as a result of urine flow through the urine flowpath, and continues to be dispensed from the sampling/flushing port and the third catheter to the first and cystostomy catheters so that the non-dynamic volume serves as an anti-infection, anti-encrustation reservoir.

2. The procedure according to claim 1, wherein the distal end of the first catheter comprises a locking loop configured to secure the distal end of the first catheter within the renal pelvis.

3. The procedure according to claim 1, wherein the distal end of the first catheter is placed within the ureter as a ureterostomy catheter.

4. The procedure according to claim 1, wherein the distal end of the cystostomy catheter comprises a locking loop configured to secure the distal end of the cystostomy catheter within the urinary bladder.

5. The procedure according to claim 1, wherein the distal end of the first catheter is secured within the renal pelvis with a cuff that is pexied to the kidney with or without a locking loop.

6. The procedure according to claim 1, wherein the distal end of the cystostomy catheter is secured within the urinary bladder with a cuff that is pexied to the urinary bladder with or without a locking loop.

7. The procedure according to claim 1, further comprising:
   inserting a needle through the skin of the patient and through the entry site; and then
   performing at least one step chosen from the group consisting of testing, sampling and flushing the ureteral bypass device.

8. The procedure according to claim 7, wherein the step comprises sampling fluid within the ureteral bypass device for infection and urinalysis while the ureteral bypass device remains implanted within the patient.

9. The procedure according to claim 7, wherein the step comprises testing the ureteral bypass device while the ureteral bypass device remains implanted within the patient by injecting a contrast material into the ureteral bypass device so that a first portion of the contrast material flows into the kidney and the urinary bladder to ensure patency and prevent occlusion and a second portion of the contrast material is retained within the non-dynamic volume of the third catheter.

10. The procedure according to claim 7, wherein the step comprises:
    determining whether an occlusion is present in the ureteral bypass device; and then
    flushing the occlusion from the ureteral bypass device with a fluid while the ureteral bypass device remains implanted within the patient, wherein a portion of the fluid is retained in the non-dynamic volume of the third catheter and is dispensed therefrom to the first and cystostomy catheters.

11. The procedure according to claim 1, further comprising:
    implanting a fourth catheter through the incision and securing a distal end of the fourth catheter within the renal pelvis of a second kidney of the patient; and then
    fluidically connecting the fourth catheter to the adapter so as to fluidically connect the fourth catheter to the cystostomy catheter.

12. The procedure according to claim 1, wherein the patient is an animal.

13. The procedure according to claim 12, wherein each of the first and cystostomy catheters has a diameter within a range of about 5 to about 30 Fr.

14. The procedure according to claim 1, wherein the patient is a child or adult human.

15. The procedure according to claim 14, wherein each of the first and cystostomy catheters has a diameter within a range of about 5 to about 8 Fr.

16. The procedure according to claim 1, wherein the ureteral bypass device remains indwelling long-term within the patient.

17. The procedure according to claim 1, further comprising:
    creating a second incision in the patient;
    disconnecting the adapter from at least one of the first and cystostomy catheters; and then
    removing one or more of the adapter and the first and cystostomy catheters but not the ureteral bypass device in its entirety.

18. A ureteral bypass device comprising:
    a first catheter having a proximal end, an oppositely-disposed distal end, and means for securing the distal end within the renal pelvis or ureter of a patient, wherein the first catheter is a nephrostomy or ureterostomy catheter;
    a cystostomy catheter having a proximal end, an oppositely-disposed distal end, and means for securing the distal end of the cystostomy catheter within the urinary bladder of the patient;
    an adapter fluidically connected to the proximal ends of the first and cystostomy catheters so as to fluidically connect the first and cystostomy catheters together through the adapter;
    a third catheter fluidically connected at a proximal end thereof to the adapter, the third catheter having an internal volume; and
    a sampling/flushing port comprising a septum and having an internal volume, the sampling/flushing port being fluidically connected to the adapter with the third catheter so that the internal volume of the third catheter is between the adapter and the sampling/flushing port;
    wherein the first and cystostomy catheters are fluidically connected together through the adapter to define a urine flowpath therethrough, the first and cystostomy catheters and the adapter are configured to be placed completely intra-abdominal, the first and cystostomy catheters and the adapter are fluidically connected to the sampling/flushing port with the adapter, the sampling/flushing port and a distal portion of the third catheter are configured to be located subcutaneously at the surface of an abdominal wall of the patient so that the septum defines an entry site that is accessible through the skin of the patient when the sampling/flushing port is subcutaneously placed to provide means for performing diagnostic and therapeutic procedures, and the internal volumes of the sampling/flushing port and the third catheter are outside the urine flowpath and define a non-dynamic volume fluidically connected to the adapter; wherein:
    urine does not flow through the non-dynamic volume; and
    at least a portion of a fluid introduced into the artificial ureteral bypass device through the entry site is retained within the non-dynamic volume outside of the urine flowpath, is not subject to being flushed through the first and cystostomy catheters as a result of urine flow through the urine flowpath, and continues to be dispensed from the sampling/flushing port and the third catheter to the first and cystostomy catheters so that the non-dynamic volume defines an anti-infection, anti-encrustation reservoir.

19. The ureteral bypass device according to claim 18, wherein the securing means of the first and cystostomy catheters are chosen from the group consisting of multi-fenestrated locking loops and cuffs adapted to be organ pexied.

20. The ureteral bypass device according to claim 18, wherein the distal end of at least one of the first and cystostomy catheters is straight and multi-fenestrated.

21. The ureteral bypass device according to claim 18, wherein each of the first and cystostomy catheters has a diameter within a range of about 5 to about 30 Fr.

22. The ureteral bypass device according to claim 18, wherein each of the first and cystostomy catheters has a diameter within a range of about 5 to about 8 Fr.

23. The ureteral bypass device according to claim 18, wherein each of the first and cystostomy catheters has a diameter within a range of about 5 to about 10 Fr.

24. The ureteral bypass device according to claim 18, further comprising a fourth catheter having a proximal end, an oppositely-disposed distal end, and means for securing the distal end of the fourth catheter within the renal pelvis or ureter of a patient, the adapter being fluidically connected to the proximal end of the fourth catheter so as to fluidically connect the fourth catheter to the cystostomy catheter through the adapter.

* * * * *